United States Patent
Vanney et al.

[11] Patent Number: 5,628,789
[45] Date of Patent: May 13, 1997

[54] APPARATUS FOR ATTACHMENT OF HEART VALVE HOLDER TO HEART VALVE PROSTHESIS

[75] Inventors: Guy P. Vanney, Blaine; Kurt D. Krueger, Stacy, both of Minn.

[73] Assignee: St. Jude Medical, Inc., St. Paul, Minn.

[21] Appl. No.: 526,528

[22] Filed: Sep. 11, 1995

[51] Int. Cl.$^6$ .................................................. A61F 2/24
[52] U.S. Cl. .................................................. 623/2
[58] Field of Search ...................................... 623/2, 900

[56] References Cited

U.S. PATENT DOCUMENTS

| | | |
|---|---|---|
| 3,546,710 | 12/1970 | Shumakov et al. |
| 3,574,865 | 4/1971 | Hamaker . |
| 3,828,787 | 8/1974 | Anderson et al. |
| 3,860,005 | 1/1975 | Anderson et al. |
| 4,655,218 | 4/1987 | Kulik et al. |
| 4,683,883 | 8/1987 | Martin . |
| 4,755,181 | 7/1988 | Igoe ............................ 623/2 |
| 4,865,600 | 9/1989 | Carpentier et al. ............. 623/2 |
| 4,932,965 | 6/1990 | Phillips ........................ 623/2 |
| 5,071,431 | 12/1991 | Sauter et al. ................. 623/2 |
| 5,163,954 | 11/1992 | Curcio et al. ................. 623/2 |
| 5,236,450 | 8/1993 | Scott ........................... 623/2 |
| 5,370,685 | 12/1994 | Stevens ........................ 623/2 |
| 5,403,305 | 4/1995 | Sauter et al. ................. 606/1 |
| 5,425,705 | 6/1995 | Evard et al. ................. 604/28 |
| 5,433,700 | 7/1995 | Peters ......................... 604/4 |

FOREIGN PATENT DOCUMENTS

| | | |
|---|---|---|
| 1690738 A1 | 11/1991 | U.S.S.R. |
| 1690739 | 11/1991 | U.S.S.R. ....................... 623/2 |
| WO94/18881 | 9/1994 | WIPO . |
| WO95/15715 | 6/1995 | WIPO . |
| WO95/17139 | 6/1995 | WIPO . |
| 9515715 | 6/1995 | WIPO .......................... 623/2 |

Primary Examiner—David H. Willse
Attorney, Agent, or Firm—Hallie A. Finucane, Esq.

[57] ABSTRACT

A device for engaging a heart valve prosthesis during implantation includes a mechanism for attaching the device to the heart valve prosthesis. The heart valve prosthesis includes a circular valve body having an annulus with a substantially annular aperture therein. At least one movable occluder is carried in the aperture and is movable between an open position and a closed position. The attachment mechanism includes a member which couples to the circular valve body thereby affixing the device to the heart valve prosthesis. The thickness of the device which extends in a direction above the heart valve prosthesis is reduced. The device is selectively removable from the heart valve prosthesis following implantation of the prosthesis in the heart tissue annulus of a patient.

4 Claims, 9 Drawing Sheets

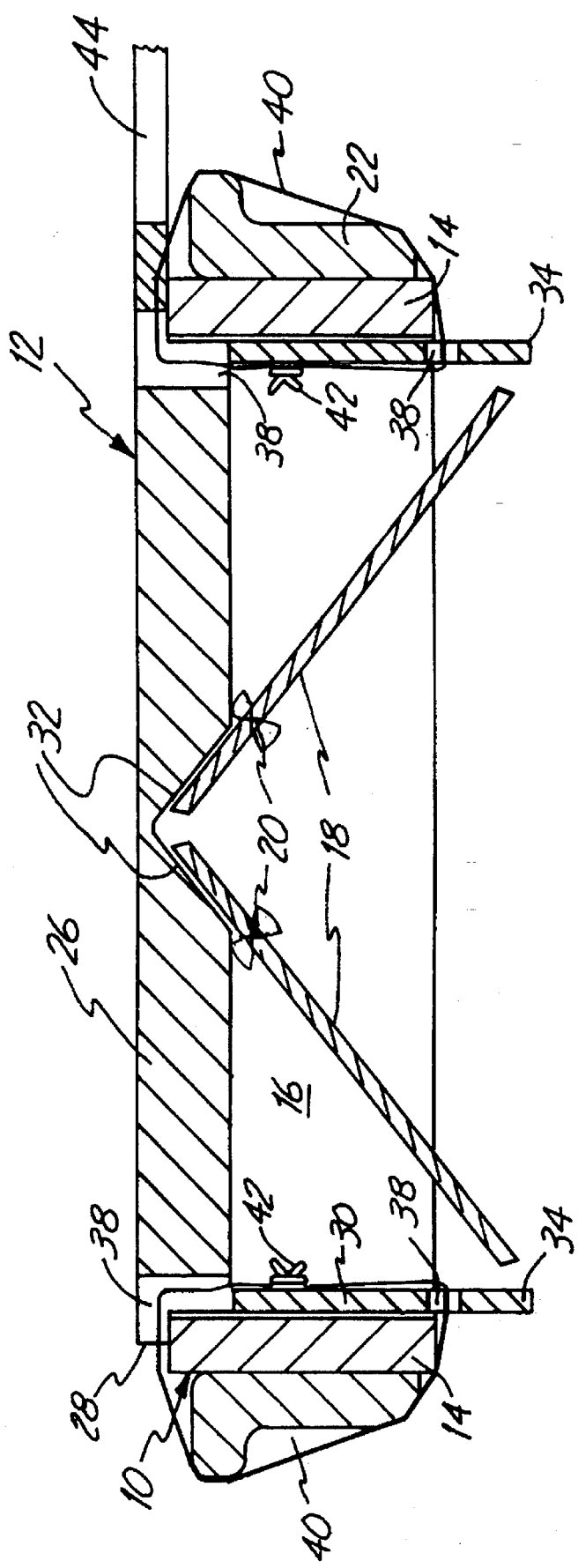

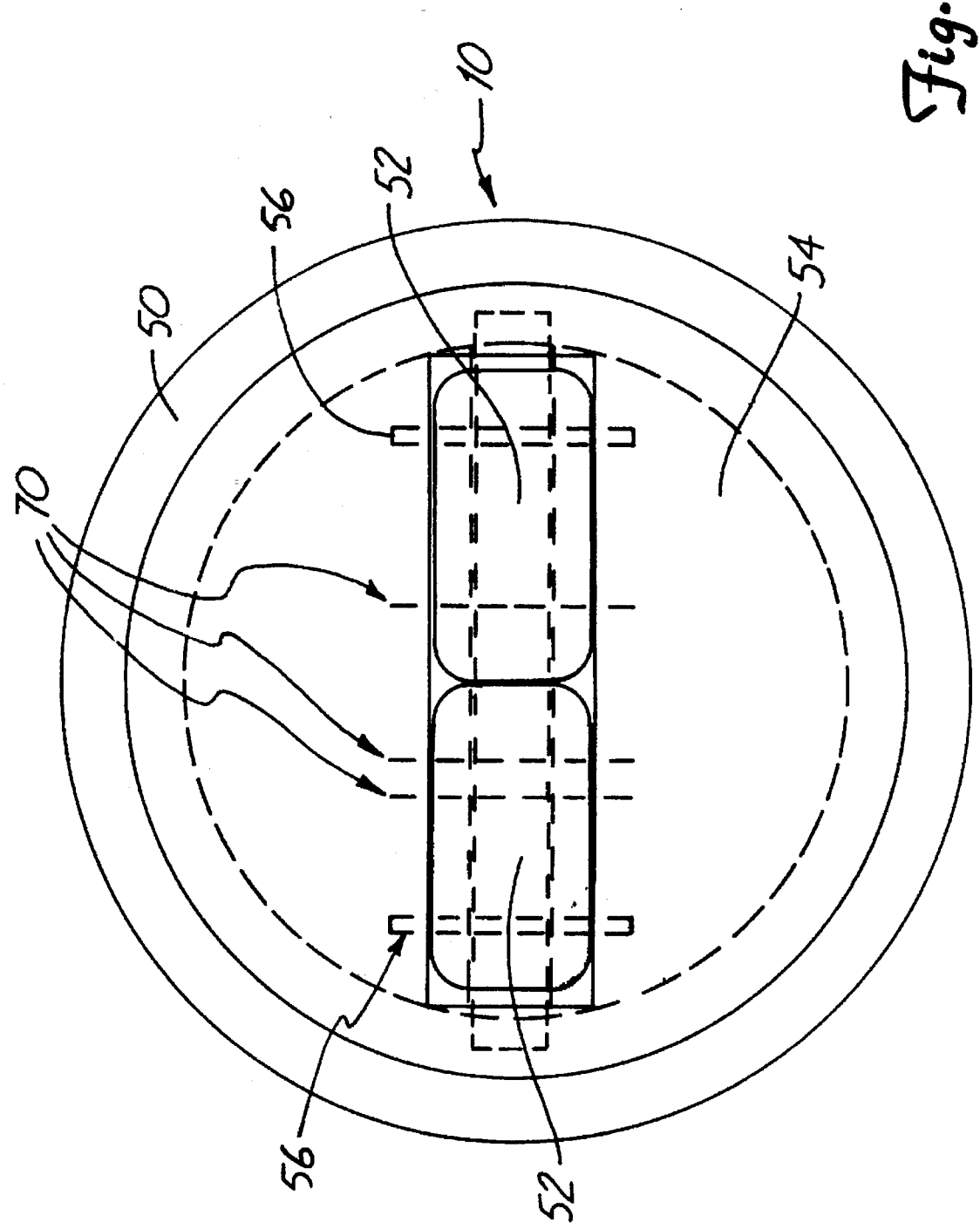

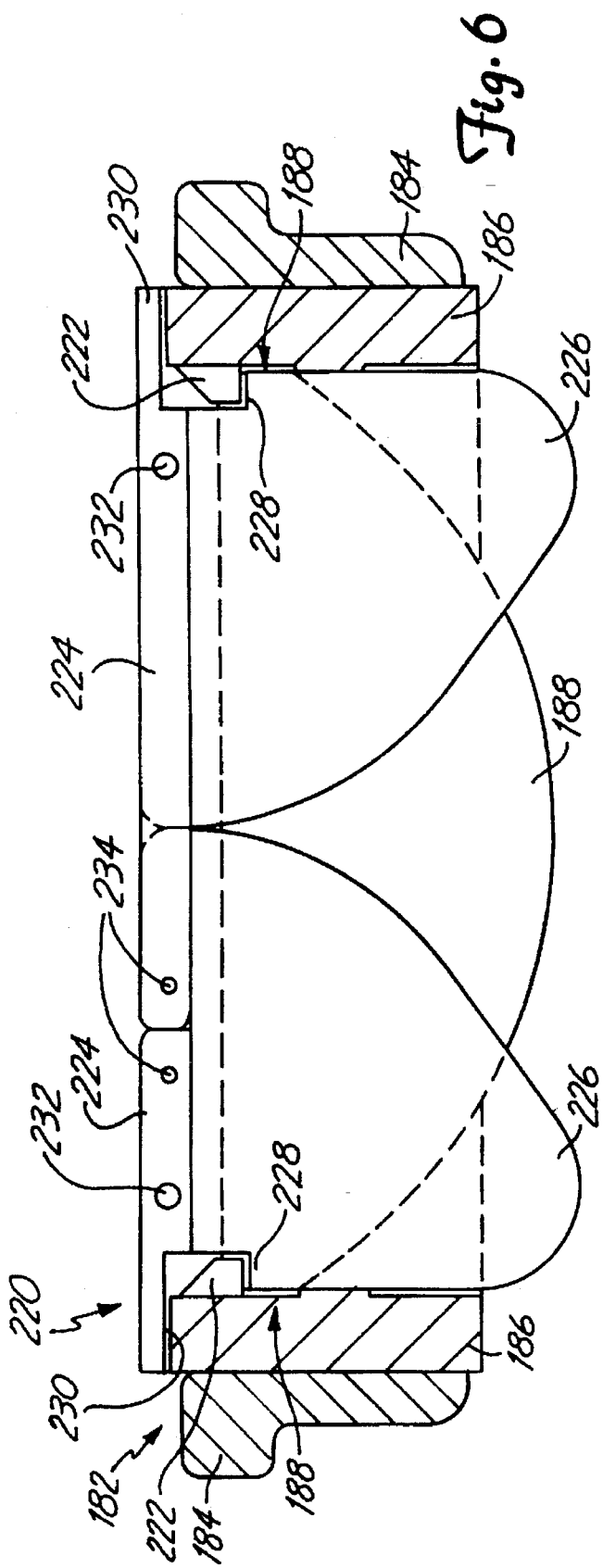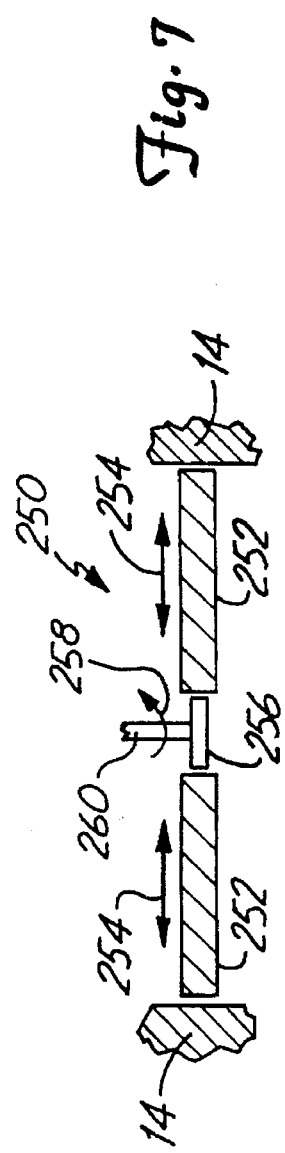

APPARATUS FOR ATTACHMENT OF HEART VALVE HOLDER TO HEART VALVE PROSTHESIS

The present invention relates to devices for implanting heart prostheses. More specifically, the invention relates to attachment of a heart valve holder to a heart valve prosthesis.

BACKGROUND OF THE INVENTION

Holders for holding heart valve prostheses during implantation are known. They are used for positioning, holding, supporting and presenting the valve during surgery. U.S. Pat. No. 3,828,787, issued Aug. 13, 1974, to Anderson et al., entitled COLLET FOR HOLDING HEART VALVE, shows a heart valve holder carried on a distal end of an elongated handle. U.S. Pat. No. 4,932,965, issued Jun. 12, 1990, to Phillips, entitled ARTIFICIAL VALVE, AND NEEDLE AND SUTURE HOLDER AND METHOD OF USING SAME, shows another heart valve holder in which the valve is held against distal ends of a pair of elongated legs during implantation.

Typically, heart valve replacement surgery is an involved procedure in which a sternotomy or thoracotomy is performed and the chest cavity of the patient must be widely opened to provide access to the patient's heart. This provides a surgeon with direct, unobstructed access to the heart. However, this procedure requires a prolonged period to recover from the trauma suffered to the upper torso.

Recently, a procedure has been developed wherein open heart surgery is performed through trocars placed in small incisions between ribs of the patient. This is described in International Publication No. WO 95/15715 entitled DEVICES AND METHODS FOR INTRACARDIAC PROCEDURES; U.S. Pat. No. 5,433,700, issued Jul. 18, 1995, to Peters, entitled METHOD FOR INTRALUMINALLY INDUCING CARDIOPLEGIC ARREST AND CATHETER FOR USE THEREIN; and U.S. Pat. No. 5,425,705, issued Jun. 20, 1995, to Evard et al., entitled THORACOSCOPIC DEVICES AND METHODS FOR ARRESTING THE HEART; and International Publication No. WO 94/18881, entitled METHOD FOR PERFORMING THORASCOPIC CARDIAC BYPASS PROCEDURES. In this procedure, elongated tools are used to operate on the heart through the trocars. As discussed in Publication No. WO 95/15715, this procedure can be used during heart valve replacement. When a heart valve prosthesis is inserted through a trocar, extreme care must be taken to protect the occluders in the valve, and once inserted, it becomes desirable to change the orientation of the valve prior to implantation to simplify the suturing of the heart valve prosthesis in place.

The trocar results in minimal rib spreading and does not involve the significant chest trauma associated with traditional open heart surgery. One advantage of this procedure is that the recovery period can be reduced significantly. Unfortunately, mechanical heart valves and the associated assembly used for implantation are large relative to the intercostal space between the ribs and are difficult to fit therethrough. Further, the heart valve holder must be securely attached to the heart valve prosthesis and yet be easily removed once the valve has been attached to the heart tissue annulus.

SUMMARY OF THE INVENTION

A device for engaging a heart valve prosthesis during implantation includes a mechanism for attaching the device to the heart valve prosthesis. The heart valve prosthesis includes a circular valve body having an annulus with a substantially annular aperture therein. At least one movable occluder is carried in the annulus and is movable between an open position and a closed position. The attachment mechanism includes a member which couples to the circular valve body, thereby affixing the device to the heart valve prosthesis at the valve body. The member is selectively removable from the valve body, thereby releasing the device from the valve body.

In one embodiment, the attachment mechanism includes a member which extends into the annulus of the heart valve prosthesis and clasps the heart valve body. One embodiment includes coupling to the heart valve body at a region where an occluder of the heart valve prosthesis connects to the heart valve body, for example proximate the pivot region of the heart valve body. The heart valve body may be engaged by the holder at a pivot or at pivot stops adjacent the occluder.

One embodiment includes moving the attachment mechanism in a horizontal direction substantially parallel with a plane of the annulus while reducing dimensions of the device in a direction perpendicular to the plane of the annulus.

BRIEF DESCRIPTION OF THE DRAWINGS

FIG. 1 is a cross-sectional view showing a heart valve prosthesis holder coupled to a heart valve prosthesis in accordance with one embodiment.

FIG. 2B is a top plan view showing the holder of FIG. 2A engaged with a heart valve prosthesis.

FIG. 6 is a cross-sectional view of a holder in accordance with another embodiment coupled to a heart valve prosthesis.

FIG. 7 is a cross-sectional view showing a cam actuated holder in accordance with another embodiment.

DETAILED DESCRIPTION OF THE PREFERRED EMBODIMENTS

Figure 2A:
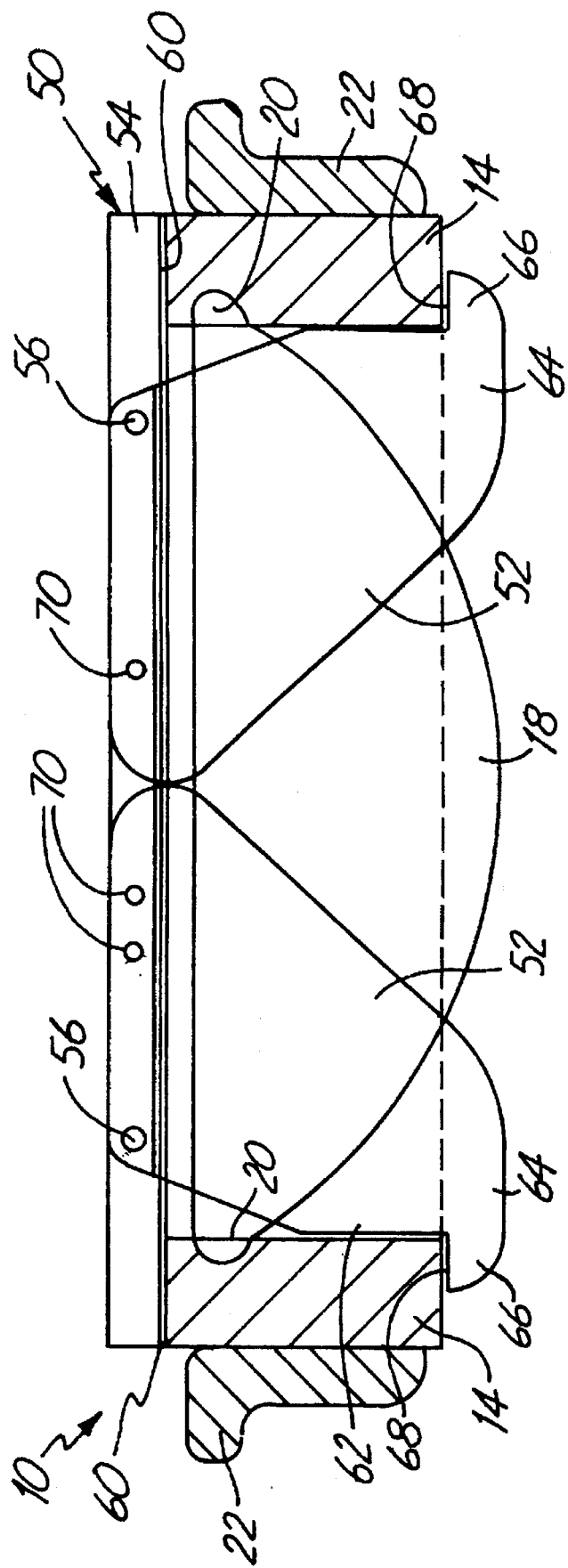
FIG. 2A is a cross-sectional view of a holder coupled to a heart valve in accordance with another embodiment.

The invention relates to attachment of a prosthetic heart valve holder to a heart valve prosthesis. The holder is used to position the heart valve prosthesis during implantation. In one embodiment, this implantation is through minimally invasive surgery such as when performed through a small trocar or similar device. The holder and valve are carried at the distal end of a handle which extends perpendicular to the axis of the valve annulus during insertion through the trocar. Reference is made to copending application Ser. No. 08/526,530 filed on Sep. 11, 1995 entitled LOW PROFILE MANIPULATORS FOR HEART VALVE PROSTHESES. For purposes of this description of the invention, the holder and attachment mechanism will be described generally. The holder and attachment mechanism may be used with any appropriate heart valve prosthesis including heart valve prostheses which are available from St. Jude Medical, Inc., of St. Paul, Minn.; Baxter Healthcare Corp., Edwards CVS Div., Irvine, Calif.; Medtronic, Inc., Minneapolis, Minn.; Shiley, Inc., Irving, Calif.; Omniscience Medical Inc., Grove Heights, Minn.; Carbomedics, Inc., Austin, Tex.; and Sorin Biomedica, Saluggia, Italy. In general, heart valve prostheses depicted herein are shown in a generic form and the scope of the present invention is intended to cover variations required to adapt the holder and attachment mechanism to different heart valve prostheses.

FIG. 1 is a cross-sectional view of a heart valve prosthesis 10 engaged with a heart valve prosthesis holder 12 in accordance with one embodiment. Heart valve prosthesis 10 includes a generally circular heart valve prosthesis body 14 having an interior annulus 16 formed therein. Occluders 18 are carried in annulus 16 and rotatably coupled to body 14 at pivots 20. Occluders 18 are movable between an open position, and a closed position in which blood flow through annulus 16 is blocked. In FIG. 1, occluders 18 are shown in a partially open position. A sewing ring or suture cuff 22 extends around the outer circumference of body 14. Although the particular heart valve prosthesis 10 has been shown in accordance with one embodiment, other heart valves may also be used with the present invention. For example, the heart valve prosthesis may include different numbers of leaflets including a single leaflet, may have a different orifice or annulus shape, or the leaflets may operate in accordance with a different mechanism.

Holder 12 includes a top member 26 having a lip 28 shaped for engaging body 14. Holder 12 also includes elongated portion 30 which extends into annulus 16 in a direction parallel with the axis of annulus 16. Portion 30 is shaped to conform generally to the inner diameter of heart valve prosthesis body 14. Holder 12 includes occluder retaining members 32 formed in top 26. Members 32 are shaped to engage occluders 18. In the embodiment shown in FIG. 1, members 32 prevent occluders 18 from opening beyond a predetermined position. This position prevents occluders 18 from extending beyond the distal portion 34 of circular portion 30 to an exposed position, thereby protecting occluders 18. Distal portions 34 of member 30 extended to or beyond occluders 18 and prevent occluders 18 from being damaged. Additionally, portions 34 prevent occluders 18 from being closed beyond a predetermined point. Holder 12 includes suture openings 38 for receiving suture(s) 40. Suture(s) 40 extend from holder 12 around heart valve prosthesis 10 generally perpendicular to the plane of the annulus 16 and generally parallel with the axis of valve 10.

In FIG. 1, an elongated handle portion 44 extends in a direction parallel to the plane of the annulus of valve 10. Handle 44 is used by a surgeon during implantation of valve 10 to manipulate valve 10 adjacent the tissue annulus formed in a patient's heart when the natural valve is excised. Suture cuff 22 is used to suture valve 10 to the heart tissue annulus by techniques known in the art. Following attachment of valve 10 to the heart tissue annulus, the surgeon cuts suture(s) 40, thereby releasing holder 12 such that holder and attached suture(s) may be removed from valve 10.

FIG. 2A is a cross-sectional view of a holder 50 in accordance with another embodiment. Holder 50 includes engagement jaws 52 coupled to top member 54 at pivots 56. Member 54 includes lip portion 60 adapted for engaging the top rim of heart valve prosthesis body 14. Jaws 52 include outer surfaces 62 which generally conform to the inner surface of body 14. Jaws 52 include distal portions 64 having distal tips 66. Distal tips 66 include interior surface 68 adapted for engaging the bottom rim of body 14. In the position shown in FIG. 2A, holder 50 holds heart valve prosthesis 10 between lip 60 of top member 54 and interior surface 68 of jaw 52.

Heart valve prosthesis 10 is releasably held by holder 50. Holder 50 is removed from prosthesis 10 by disengaging tip members 66 of jaws 52 from body 14. Disengagement of tip members 66 is performed by rotating jaws 52 about pivots 56. Jaws 52 are held in a closed position by sutures (not shown) which extend through suture holes 70.

FIG. 2B is a top plan view showing holder 50 engaged with prosthesis 10. In operation, following attachment of prosthesis 10 to the heart tissue annulus, holder 50 is removed by cutting the sutures which extend through suture holes 70. A third suture hole 70 is provided to secure the suture (not shown) to a jaw 52 after the suture has been cut such that the suture is removed with holder 50. After the suture has been cut, jaws 52 are free to pivot about pivots 56, allowing distal tips 66 of jaws 52 to disengage from body 14. In another embodiment which is not shown, two pairs of jaws 52 are adjacent occluders 18.

Figure 3A:
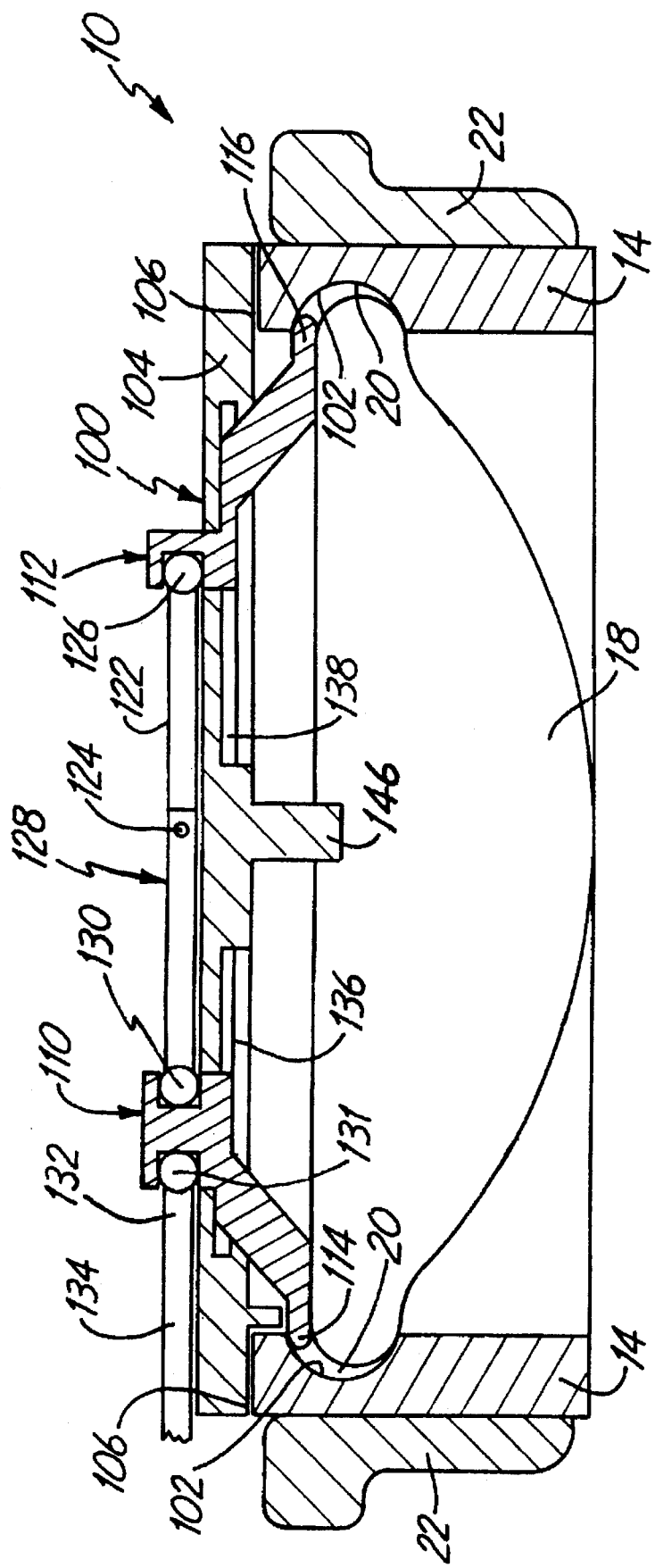
FIG. 3A is a side cross-sectional view of a holder in accordance with another embodiment engaged with a heart valve prosthesis.
Figure 3B:
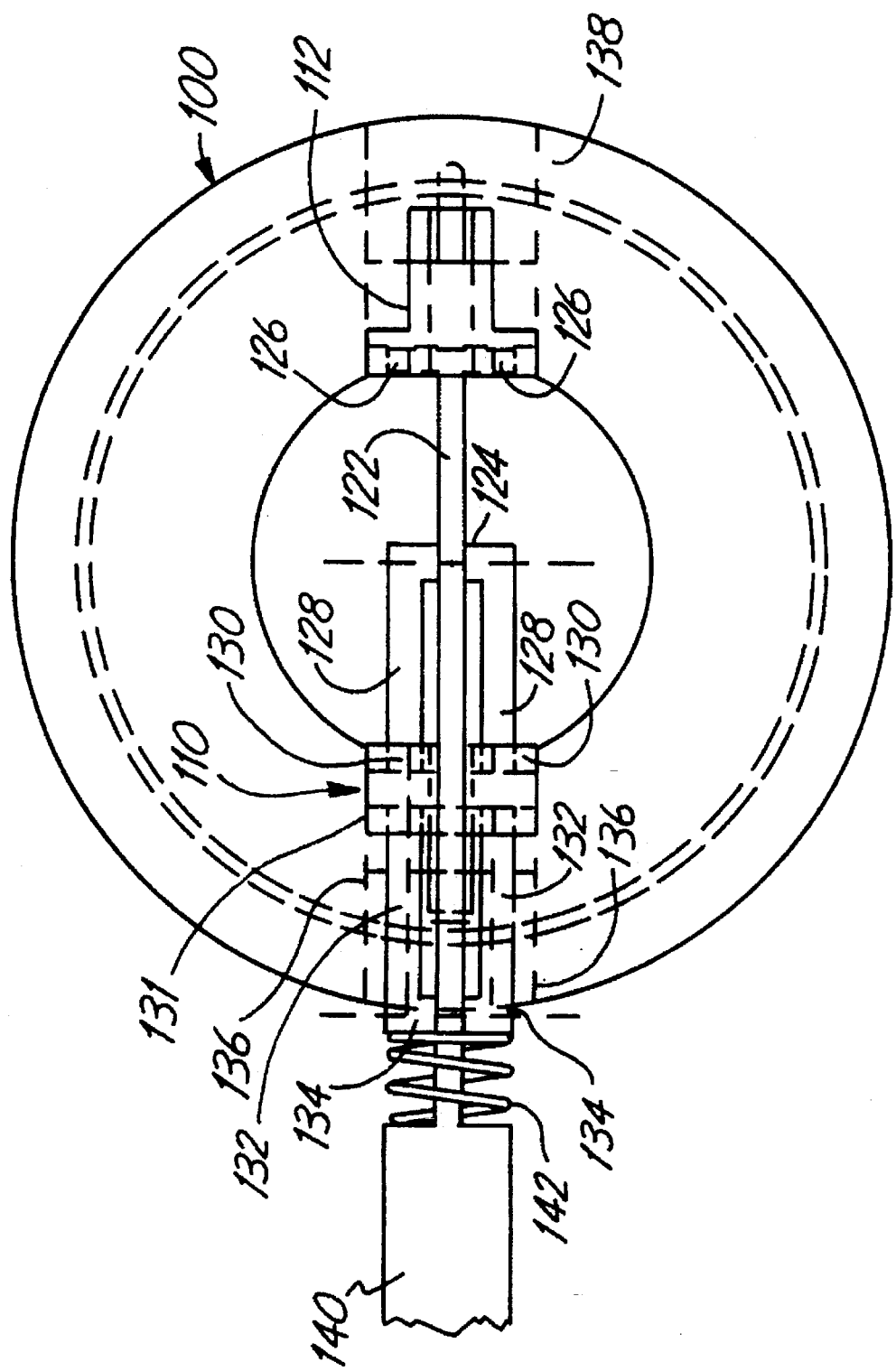
FIG. 3B is a top plan view of the embodiment of FIG. 3A.

FIG. 3A is a side cross-sectional view of heart valve prosthesis 10 engaged with holder 100 in accordance with another embodiment. Holder 100 is adapted for coupling to recesses 102 of pivots 20. Holder 100 includes top member 104 having lip 106 which engages body 14 of prosthesis 10. Sliding members 110 and 112 include engaging tips 114 and 116 which conform to recesses 102. Holder 100 couples to handle link 128 which is also shown in FIG. 3B. Link 128 attaches to distal link 122 at pivot 124. Link 128 attaches to sliding member 112 at pivot 126. Links 128 attach to sliding member 110 at pivots 130 and to pivot 124. Links 122 are attached to links 132 at pivots 134. Guide 136 allows guiding of sliding member 110 during engagement and disengagement of holder 10. Guide 138 in FIG. 3A allows sliding member 112 to slide therein. An elongated handle 140 shown in FIG. 3B attaches to holder 100 at pivots 126, 130 and 131 and is spring loaded by spring 142.

In operation, prosthesis 10 is released from holder 100 by urging handle 140 in a direction toward holder 100. This causes pivot 124 to move in an upward direction away from holder 100 causing sliding members 110 and 112 to slide together in an inward direction by disengaging tips 114 and 116 from recesses 102. After tips 114 and 116 have been disengaged, holder 100 may be removed from valve 10. In the engaged position, valve 10 is held between lip 106 and engaging tips 114 and 116. Occluders 18 are held in a closed, or nearly closed, position by occluder engaging member 146. Engaging member 146 may be made out of any suitable material which is compatible with occluders 18, including polytetrafluoroethylene (PTFE) felt, soft polymer or any other suitable biocompatible material.

Figure 4:
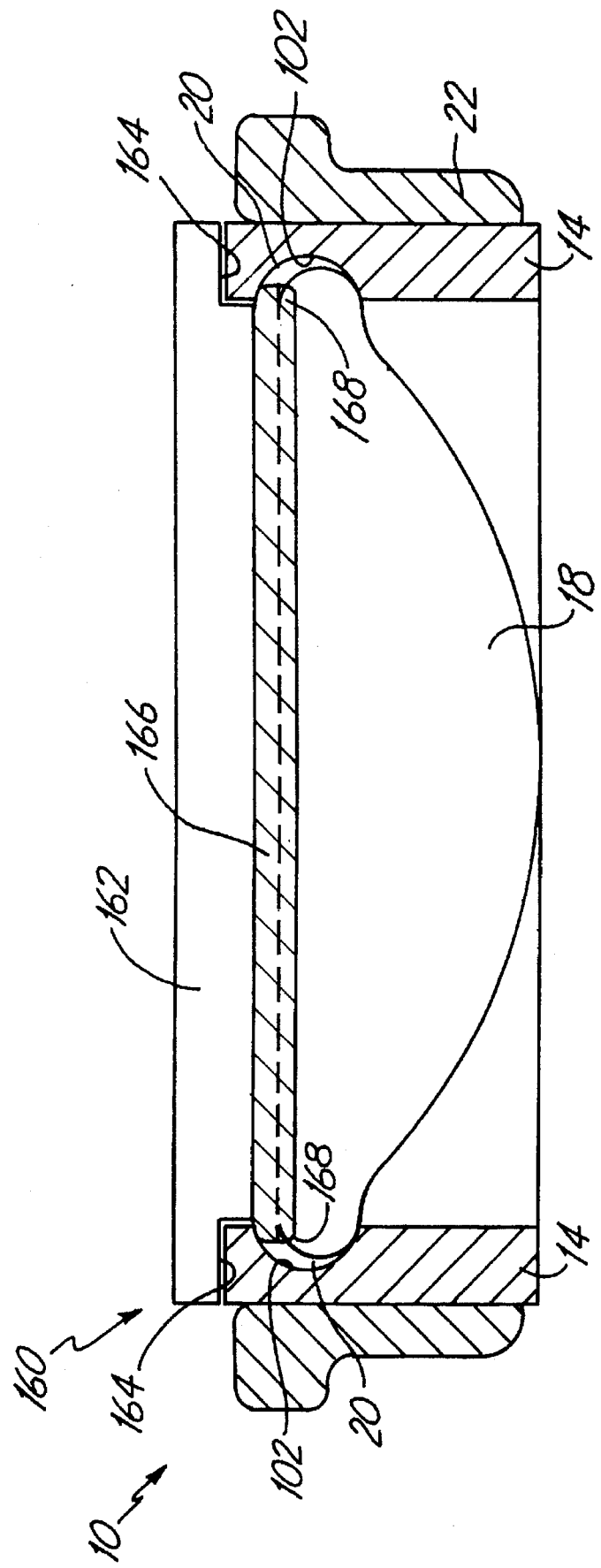
FIG. 4 is a cross-sectional view of a holder in accordance with another embodiment engaged with a heart valve prosthesis.

FIG. 4 is a cross-sectional view of holder 160 engaged with recesses 102 of pivots 20 of heart valve prosthesis 10. Holder 160 includes top member 162 having lip 164 which engages the top rim of body 14 of prosthesis 10. A compliant member 166 is attached to holder 160 and includes engaging tips 168 to maintain closed position of occluders. Engaging tips 168 are adapted to extend into recesses 102 of pivots 20. Heart valve prosthesis 10 is captured by lip 164 and engaging tips 168 of holder 160. Member 166 may be formed of any appropriate material which does not damage pivots 20 or occluders 18, including compliant materials such as silicone. Holder 160 is removed from valve 10 by simply forcing the holder and valve apart such that tips 168 come free from recesses 102. In another embodiment, not shown, engaging tips 168 are hollow thus allowing them to be engaged by inflation or deflation.

Figure 5A:
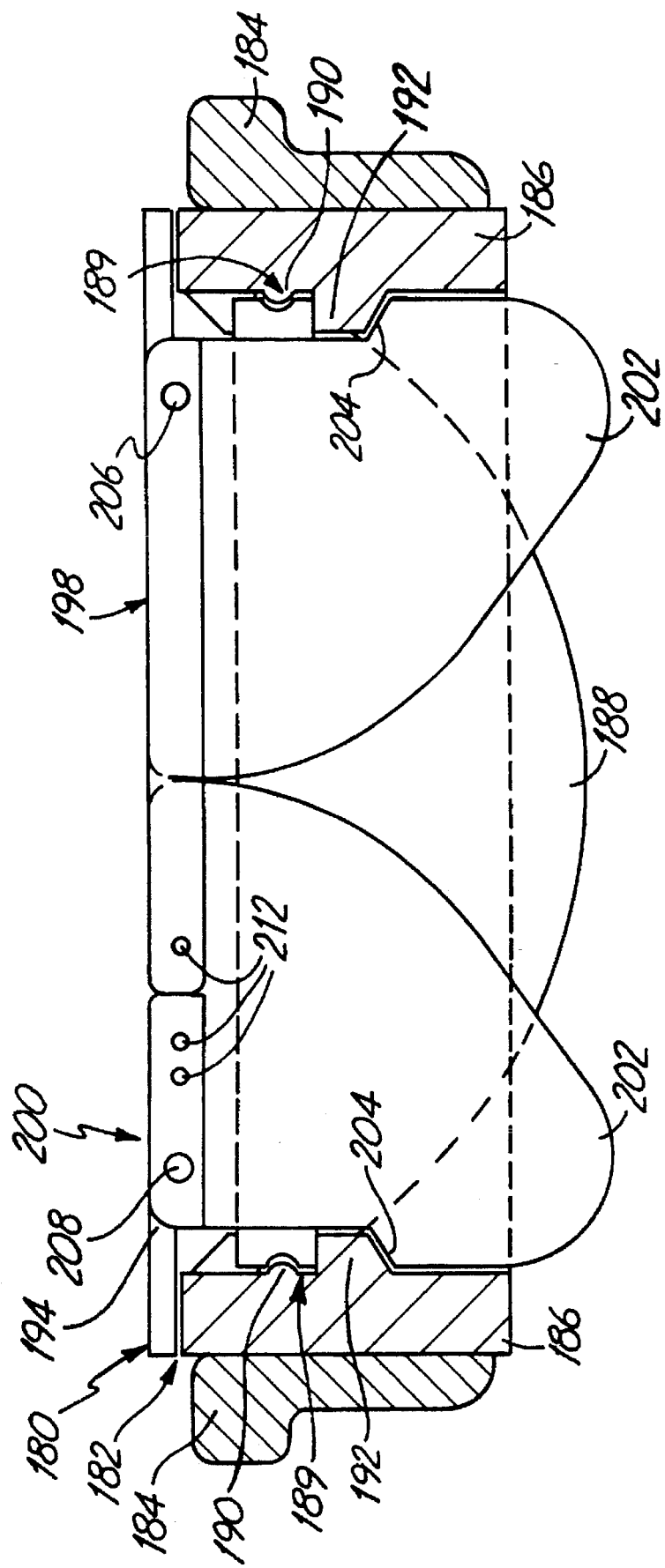
FIG. 5A is a cross-sectional view of a holder in accordance with another embodiment engaged with a heart valve prosthesis.

FIG. 5A is a cross-sectional view of a holder 180 coupled to a heart valve prosthesis 182 in accordance with another embodiment. Heart valve prosthesis 182 is an example of another type of heart valve prosthesis which includes elements in the pivot area which extend in an inward direction from the body of the heart valve prosthesis. For example, these may be pivot stops which stop movement of the occluders. Heart valve prosthesis 182 includes suture cuff 184 and heart valve prosthesis body 186. Movable occluders 188 are carried within heart valve prosthesis body 186 and pivot about pivots 189. Pivots 189 include pivot protrusions 190 which engage occluders 188 and pivot stops 192. Pivot stops 192 stop motion of occluders 188 at a predetermined point. In accordance with one aspect of the invention, pivot stops 192 are also used for coupling holder 180 to heart valve prosthesis 182.

Figure 5B:
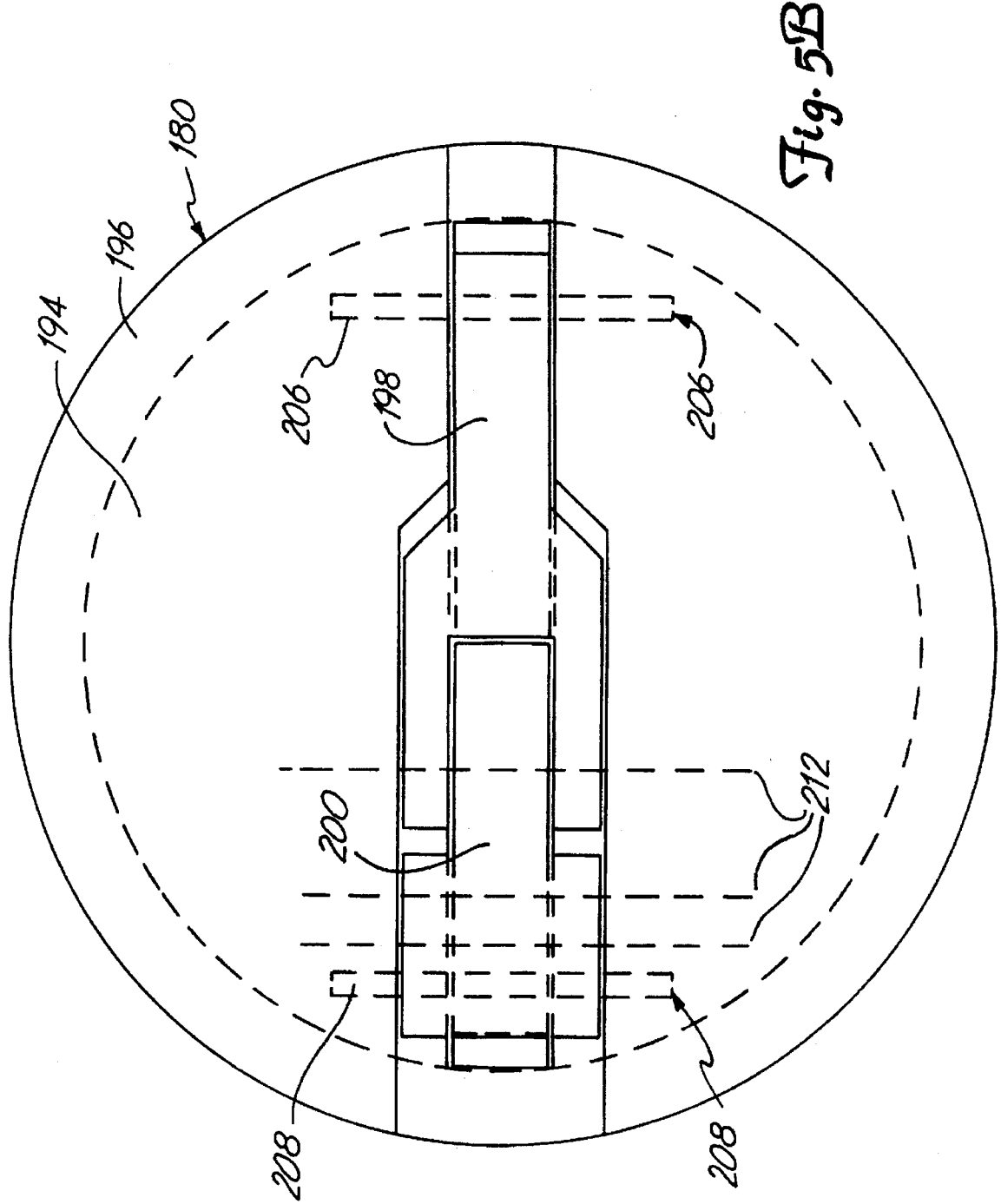
FIG. 5B is a top plan view of the holder of FIG. 5A.

Holder 180 includes top member 194 having lip 196 shown in FIG. 5B. Engagement members 198 and 200 include distal ends 202 and stop engagement portions 204 which generally conform to pivot stops 192. Member 198 is coupled to top member 194 at pivot 206 and member 200 is coupled to top member 194 at pivot 208. Suture holes indicated at 212 are provided for a suture (not shown) which is used to lock holder 180 in the closed position shown in FIGS. 5A and 5B. Holder 180 is removed from prosthesis 182 by cutting the suture (not shown) and rotating members 198 and 200 upward about pivots 206 and 208, respectively. This movement frees pivot stops 192 from engagement portions 204 such that heart valve prosthesis 182 is released. Portions 202 protect occluders 188 from damage.

FIG. 6 is a cross-sectional view of a heart valve holder 220 in accordance with another embodiment coupled to heart valve prosthesis 182. Heart valve prosthesis 182 shown in FIG. 6 is similar to prosthesis 182 of FIG. 5A except that it is shown rotated 180° such that pivot stops 222 are exposed. Holder 220 includes engaging jaws 224 which include distal ends 226. Jaws 224 are adapted to be received in heart valve prosthesis body 186 and include engagement lips 228 which engage pivot stops 222. Top member 221 includes lips 230 which engage the upper rim of heart valve prosthesis body 186. Members 224 are coupled to a top member 221 at pivots 232. Members 224 are held in the closed position shown in FIG. 6 with a suture (not shown) which extends through suture holes 234. Holder 220 is disengaged from prosthesis 182 by removing the suture (not shown) through suture holes 234 and pivoting members 224 about pivots 232 such that pivot stops 222 are released.

In accordance with another embodiment, a holder may be attached to the pivot stops shown in heart valve prosthesis 182 in FIGS. 5A and 6 using a suture which extends around the pivot stops thereby securing the holder to the pivot stops.

FIG. 7 is a cross-sectional view illustrative of cam actuated holder 250. Cam actuated holder 250 includes members 252 which move in a lateral direction indicated by arrows 254 relative to heart valve prosthesis body 14. A cam 256 is positioned between members 252. Cam 256 has an outer width which varies around its circumference such that when cam 256 is rotated in the direction shown by arrow 258, members 252 are urged against heart valve prosthesis body 14. Cam 256 is rotated using shaft 260. Holder 250 is removed from heart valve prosthesis body 14 by rotating cam 256 to a position allowing members 252 to move inward relative to heart valve prosthesis body 14 whereby holder 250 is freed from heart valve prosthesis body 14. The cam actuated holder 250 of FIG. 7 is illustrative of a cam which may be applied to the embodiments of FIGS. 3A/B and 5A/B. The cam is an example of another mechanism to provide lateral motion to portions of the holder which thereby engage onto the heart valve prosthesis body.

As used herein, attachment mechanism is used to mean a mechanism for attaching to the valve body. The preferred embodiments set forth a number of attachment mechanisms. However, the term "attachment mechanism" is intended to describe any other mechanism for attaching a valve to a valve body which is within the scope of the invention.

The present invention provides a technique for gripping a heart valve prosthesis using a low profile holder. The holders are typically attached to an elongated handle for use during implantation. The low profile holder may be selectively removed following attachment of the heart valve prosthesis to the heart tissue annulus. In the embodiments shown, the holder extends above the heart valve prosthesis a distance which is less than the total thickness of the heart valve prosthesis. Further, when the holder is attached, protrusion of the holder above the prosthesis is minimized. Designs include holding the occluders in a closed or semi-closed position and providing protection of the occluders if they extend below the bottom of the orifice of the heart valve prosthesis. In some embodiments, the valve body is held through axial forces applied substantially parallel to the valve axis. The concepts set forth may be used with both aortic and mitral valves and are useful for minimally invasive surgery techniques.

Although the present invention has been described with reference to preferred embodiments, workers skilled in the art will recognize that changes may be made in form and detail without departing from the spirit and scope of the invention.

What is claimed is:

1. An apparatus for holding a heart valve prosthesis during implantation, the heart valve prosthesis including a heart valve prosthesis body forming an annulus carrying a movable occluder therein, the apparatus comprising:

a low profile holder body having an engaging side including a lip portion for abutting the heart valve prosthesis body and a top substantially flat side opposite the engaging side, the holder body sized to extend above the heart valve prosthesis body a distance which is less than a thickness of the heart valve prosthesis body;

an interior surface of the holder body substantially conforming to the moveable occluder when the moveable occluder is in a closed position, thereby maintaining the moveable occluder in a substantially closed position such that the prosthesis body protects the moveable occluder during implantation;

an elongated portion coupled to the holder body sized to extend into the annulus of the prosthesis body and generally conform to the annulus thereby positioning the holder adjacent the prosthesis body; and at least one suture opening in the holder body for receiving a suture therethrough with the suture extending around the prosthesis body to thereby secure the heart valve prosthesis to the holder body.

2. The apparatus of claim 1 wherein the elongated portion includes a suture hole for receiving the suture therethrough.

3. The apparatus of claim 1 wherein the elongated portion includes a distal portion sized to extend beyond an edge of the prosthesis body opposite the lip portion, the distal portion providing additional protection to the moveable occluder.

4. The apparatus of claim 1 wherein the apparatus includes a second suture opening for receiving a second suture therethrough which extends around the prosthesis body to secure the heart valve prosthesis to the holder body.

* * * * *